United States Patent
Jan et al.

(10) Patent No.: US 8,350,106 B2
(45) Date of Patent: Jan. 8, 2013

(54) SELECTIVE HYDROGENATION OF UNSATURATED ALIPHATIC HYDROCARBONS IN PREDOMINANTLY AROMATIC STREAMS

(75) Inventors: Deng-Yang Jan, Elk Grove, IL (US); Michael A. Schultz, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 1227 days.

(21) Appl. No.: 12/165,291

(22) Filed: Jun. 30, 2008

(65) Prior Publication Data

US 2009/0326291 A1    Dec. 31, 2009

(51) Int. Cl.
*C07C 5/05* (2006.01)

(52) U.S. Cl. .................................. 585/259; 585/258

(58) Field of Classification Search .............. 585/258, 585/259, 250
See application file for complete search history.

(56) References Cited

U.S. PATENT DOCUMENTS

| | | | | |
|---|---|---|---|---|
| 577,686 A * | 2/1897 | Gajda | ...................... | 210/272 |
| 3,670,041 A * | 6/1972 | Juhl et al. | .................... | 585/258 |
| 4,175,033 A | 11/1979 | Hilfman | | |
| 4,202,758 A | 5/1980 | O'Hara et al. | | |
| 4,225,418 A | 9/1980 | Hilfman | | |
| 4,571,442 A * | 2/1986 | Cosyns et al. | ................ | 585/261 |
| 4,716,256 A * | 12/1987 | Johnson et al. | ............... | 585/274 |
| 4,734,540 A | 3/1988 | Gattuso et al. | | |
| 5,004,851 A * | 4/1991 | Durham et al. | ............... | 585/260 |
| 5,352,848 A | 10/1994 | Cottrell | | |
| 5,414,183 A | 5/1995 | Abrevaya et al. | | |
| 5,516,965 A | 5/1996 | Hershkowitz et al. | | |
| 5,523,271 A * | 6/1996 | de Agudelo et al. | ............ | 502/74 |
| 5,658,453 A * | 8/1997 | Russ et al. | ..................... | 208/62 |
| 5,675,041 A | 10/1997 | Kiss et al. | | |
| 5,744,686 A * | 4/1998 | Gajda | .......................... | 585/823 |
| 5,821,397 A * | 10/1998 | Joly et al. | ..................... | 585/262 |
| 5,877,364 A * | 3/1999 | Hernandez et al. | ........... | 585/262 |
| 5,981,818 A | 11/1999 | Purvis et al. | | |
| 6,339,182 B1 | 1/2002 | Munson et al. | | |
| 6,623,659 B2 | 9/2003 | Munson et al. | | |
| 6,689,926 B2 * | 2/2004 | Merrill | ......................... | 585/259 |
| 6,781,023 B2 * | 8/2004 | Brown et al. | ................. | 585/276 |
| 6,824,674 B2 * | 11/2004 | Kaminsky | ..................... | 208/143 |
| 6,949,686 B2 | 9/2005 | Kaminsky | | |
| 7,060,852 B2 | 6/2006 | Maas et al. | | |
| 7,744,750 B2 * | 6/2010 | Brown et al. | ................. | 208/299 |
| 7,777,086 B2 * | 8/2010 | Hwang et al. | ................. | 585/448 |

(Continued)

OTHER PUBLICATIONS

Nadkarni, Guide to ASTM Test Methods for the Analysis of Petroleum Products and Lubricants, 2nd ed., ASTM International, 2007, month unknown.*

*Primary Examiner* — In Suk Bullock
*Assistant Examiner* — Bradley Etherton
(74) *Attorney, Agent, or Firm* — Mark R Willis

(57) ABSTRACT

The selective saturation of unsaturated aliphatic hydrocarbons (e.g., diolefins) in a hydrogenation feed stream comprising an aromatic compound (e.g., benzene) and one or more nitrogen compounds renders it beneficial when the stream or a portion thereof is subsequently treated (e.g., with a zeolitic adsorbent) to remove nitrogen. In particular, the selective saturation of, for example, olefins and diolefins prolongs the life of the nitrogen guard bed. In a representative embodiment, the selective hydrogenation is applied to a recycle benzene-containing stream recovered in the separation section (e.g., from the benzene/toluene splitter overhead) of a styrene production process, prior to treatment with a nitrogen guard bed adsorbent.

18 Claims, 1 Drawing Sheet

U.S. PATENT DOCUMENTS

| | | |
|---|---|---|
| 2002/0175108 A1 | 11/2002 | Debuisschert et al. |
| 2002/0193649 A1 | 12/2002 | O'Rear et al. |
| 2004/0254411 A1 | 12/2004 | Steinbrenner et al. |
| 2005/0143612 A1 | 6/2005 | Hwang et al. |
| 2005/0152819 A1 | 7/2005 | Schmidt et al. |
| 2005/0209491 A1 | 9/2005 | Ryu |
| 2006/0167308 A1 | 7/2006 | Maas et al. |

* cited by examiner

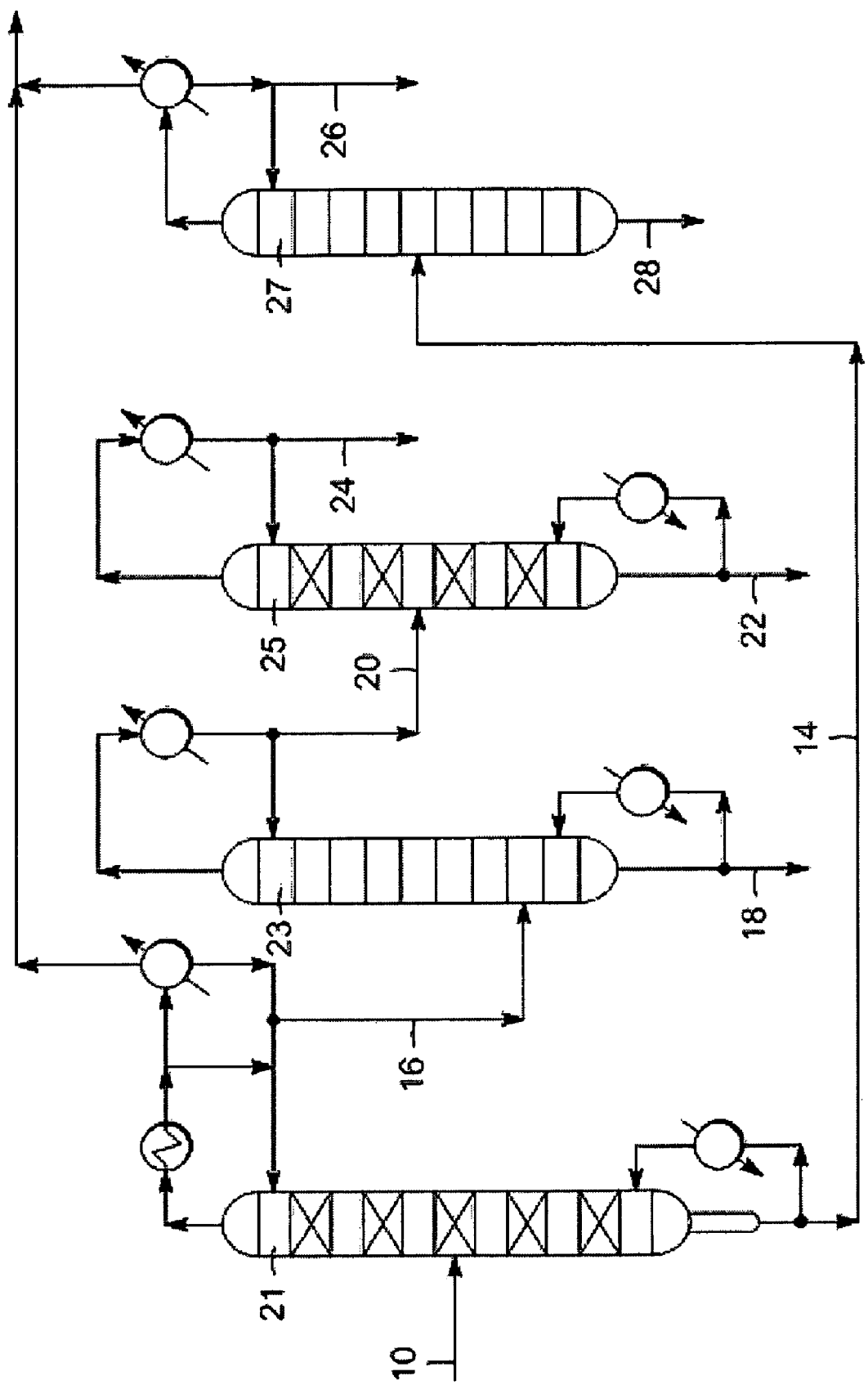

SELECTIVE HYDROGENATION OF UNSATURATED ALIPHATIC HYDROCARBONS IN PREDOMINANTLY AROMATIC STREAMS

FIELD OF THE INVENTION

The present invention relates to methods for the selective saturation of unsaturated aliphatic hydrocarbons such as straight chain and branched $C_4$-$C_6$ diolefins, present in liquid streams and particularly benzene streams that may be recovered in the downstream separation section of a process for the production of styrene from ethylbenzene.

DESCRIPTION OF RELATED ART

Styrene (phenylethylene, vinylbenzene), an important monomer used in the manufacture of many plastics, is commonly produced in a two-step process. First, ethylbenzene (EB) is formed by alkylating benzene, by transalkylating polyethylbenzenes (PEBs), or by both. The EB is then dehydrogenated, in the presence of steam (which supplies the sensible heat needed for the endothermic reaction), to produce styrene. The EB dehydrogenation effluent (or crude styrene product) is then processed in a separation section, typically using three of four distillation columns, to recover purified styrene monomer, unreacted EB and benzene, as well as byproduct benzene and other byproducts, namely toluene, and heavies (tar). Distillation trains, used in separation sections to recover these components, for commercial EB dehydrogenation effluents are described, for example, in U.S. Pat. No. 3,409,689 and U.S. Pat. No. 3,525,776.

In a representative distillation scheme, the EB dehydrogenation effluent is sent to a first, ethylbenzene/styrene distillation column (or EB/styrene splitter) that separates or splits the EB dehydrogenation effluent into (i) EB and lighter components in its overhead and (ii) styrene and heavier components in its bottoms. A second column, generally referred to as EB recovery column, then separates the EB/styrene splitter overhead into (i) benzene and toluene in its overhead and (ii) EB in its bottoms for recycle to the dehydrogenation reactor. A third column, namely a benzene/toluene splitter, separates the EB recovery column overhead into (i) benzene in its overhead and (ii) toluene its bottoms. A fourth column can be used to further purify styrene, in the EB/styrene splitter bottoms, from a heavy fraction.

Various other distillation trains for processing the EB dehydrogenation effluent are possible. For further information and examples, see U.S. Pat. No. 3,525,776 and U.S. Pat. No. 4,252,615; Ullmann's Encyclopedia of Industrial Chemistry, 5$^{th}$ Edition, Vol. A25, VCH Publishers, New York, USA, 1994, at pages 329-344; Encyclopedia of Chemical Processing and Design, Vol. 55, Marcel Dekker, Inc., New York, USA, 1996, at pages 197-217; the technical sheet entitled "Lummus/UOP Classic SM Process," UOP LLC, Des Plaines, Ill., USA, 1997; and the technical sheet, "Ethylbenzene/'Classic' Styrene Monomer," ABB Lummus Global, Bloomfield, N.J., USA, Mar. 29, 2001.

Normally, the benzene in the EB dehydrogenation effluent of the styrene production process is primarily recovered as a benzene/toluene splitter overhead stream, as discussed with respect to the representative distillation scheme above. In some cases, the benzene may be contained in a combined benzene-toluene fraction, for example as an EB recovery column overhead stream, which is not processed further to separate the benzene from the toluene. Alternatively, the benzene from the EB dehydrogenation effluent may be contained in various other streams, depending on the particular separation scheme used.

Regardless of the ultimate destination of the benzene, the amount produced as a byproduct, due to non-selective cracking in the EB dehydrogenation reactor, is relatively small. However, benzene that is unconverted in the EB alkylation reactor also contributes to the total benzene in the EB dehydrogenation effluent. Still more benzene may be recovered in cases where styrene producers choose to introduce benzene to the EB dehydrogenation reactor, as described, for example, in U.S. Pat. No. 3,409,689 and U.S. Pat. No. 3,525,776. Therefore, after benzene is recovered in any of a number of possible streams of a distillation train fed by the EB dehydrogenation effluent, it is generally economically beneficial to recycle the benzene-containing stream (e.g., the overhead stream of the benzene/toluene splitter) as a reactant to the benzene alkylation reaction, used in the first step of the styrene production process, as discussed above.

While the distillation flow schemes for separating the EB dehydrogenation effluent are straightforward, certain known difficulties must be addressed. One of these is corrosion, which stems from the use of steam in the EB dehydrogenation reaction and ultimately promotes the condensation of acidic aqueous solutions in the cooler overhead sections of the distillation columns. Another difficulty is auto-polymerization of styrene in the hotter sections of the columns, typically from about 90° C. (195° F.) to about 150° C. (300° F.).

To prevent corrosion and polymerization, small amounts of inhibitors are added to the EB dehydrogenation effluent and/or the distillation train. The optimum choice of inhibitor(s) involves weighing many factors besides inhibition effectiveness, including cost, availability, volatility, toxicity, thermal stability, solubility, viscosity, the presence of oxygen, and the nature of the resultant residue. While individual styrene production plants may use different inhibitors, most if not all currently in operation use at least one inhibitor. The exact chemical compositions of inhibitors in commercial use are not widely known, except to the commercial suppliers of these inhibitors. However, since the chemistry of both corrosion and polymerization is well understood, certain general characteristics of these inhibitors are well known.

For example, it is generally known that many corrosion inhibitors and polymerization inhibitors are nitrogen compounds, including acetonitrile and other reactive nitriles. With respect to corrosion inhibitors, other types of nitrogen compounds include primary, secondary, and tertiary amines, as well as diamines (e.g., ethylene diamine), triamines, and their substituted derivatives, in which possible nitrogen atom substituents include alkyl or hydroxyalkyl groups. Ethanolamine and diethanolamine may also be in use. Possible classes of nitrogen compounds used for corrosion inhibition include amides, N-(acyloxy)-alkane amines, dihydro-1-alkyl-N-substituted imidazoles (e.g., dihydro-1-alkyl-N-hydroxyalkaneimidazoles and dihydro-1-alkyl-N-aminoalkane-imidazoles), trialkylaminium dialkyl phosphates, and trialkylaminium alkyl hydrogen phosphates.

Polymerization inhibitors that are nitrogen compounds include amino- and nitro-substituted aromatic compounds such as phenylenediamines, dinitrophenols, and dinitrocresols. Aromatic compounds having nitroso groups are other possible polymerization inhibitors. The background of U.S. Pat. No. 6,395,943 summarizes the extensive art relating to compounds for use as corrosion inhibitors. These include N,N-nitroso-methylaniline; N-nitrosodiphenyl amine in combination with dinitro-o-cresol; N-nitroso aniline derivatives; a mixture of dinitro-p-cresol and N-nitroso-diphenyl amine; alkyl substituted p-nitroso phenol in combination with p-nitroso phenol; N-nitrosophenyl-hydroxylamine plus hydroquinone monomethyl ether; a phenylene-diamine compound plus a hydroxyalkylhydroxyl-amine compound; 1-oxy-2,2,6,6-tetramethylpiperidine plus an aromatic nitro compound; a phenylenediamine compound plus a hindered phenol compound; the reaction product of a $C_9$-$C_{20}$ alkyl phenol with sulfuric and nitric acid and optionally an aryl or alkyl-substituted phenylenediamine; 3,5-di-tert-butyl-4-hydroxy-N,N-dimethyl benzyl amine; 4-acetylamino-2,2,6,6-tetramethyl piperidine N-oxyl in combination with 4-nitroso phenol; phosphite compounds, nitrosoamine compounds or phenol compounds; the ammonium salt of N-nitrosophenyl hydroxylamine; nitrosophenols plus dicyclohexyl-ammonium nitrate; substituted nitrosobenzene; p-nitroso phenol plus p-t-butyl catechol; N-nitroso compound, e.g., N-nitrosodiphenylamine and a catechol, e.g., p-t-butylcatechol; and N-nitroso derivates of unsubstituted or dialkyl substituted phenylenediamine. A mixture of at least one nitroso compound such as N,N'-di-2-butyl-N,N'-dinitroso-1,4-diaminobenzene and a dinitrophenol compound such as dinitrocresol, and optionally a stabilizer compound such as an N,N'-dialkyl substituted 1,4-diaminobenzene, is described in U.S. Pat. No. 6,395,943.

Corrosion inhibitors are typically added into the upper portions or overhead sections of the distillation columns, such as those discussed above (e.g., the EB/styrene splitter, the EB recovery column, and/or the benzene/toluene splitter). When polymerization inhibitors are used, they are typically added to distillation streams containing styrene or distillation columns processing styrene. Polymerization inhibitors are generally added to the EB dehydrogenation effluent stream flowing to the first distillation column in the distillation train. Further information on the use of specific polymerization inhibitors in styrene production is found in Journal of Polymer Science: Part A: Polymer Chemistry, Vol. 26, 2853-2858 (1988); U.S. Pat. No. 5,869,717; U.S. Pat. No. 4,252,615; Ullmann's Encyclopedia of Industrial Chemistry, Encyclopedia of Chemical Processing and Design, the UOP LLC technical sheet, and the ABB Lummus Global technical sheet.

Nitrogen compounds, introduced to inhibit corrosion and polymerization in the separation section of styrene production processes, are therefore unavoidably present in the separated product streams, including the benzene stream for recycle back to the benzene alkylation reactor (or reaction zone), as discussed above. These nitrogen compounds, even in trace amounts that contribute on the order of only 1 ppm nitrogen by weight, adversely affect the activity of the catalyst used in the benzene alkylation reactor, thereby resulting in more frequent plant shutdowns. The problem of rapid deactivation or poisoning of the benzene alkylation catalyst is discussed in U.S. Pat. No. 7,276,636.

The art has therefore sought to deal with the problem of nitrogen contamination of benzene-containing recycle streams to the benzene alkylation reactor. A commonly used approach involves the use of a zeolitic or molecular sieve guard bed to treat such nitrogen-contaminated streams and substantially remove the nitrogen upstream of the benzene alkylation catalyst bed. Guard beds for nitrogen removal are described, for example, in U.S. Pat. No. 7,205,448. These guard beds themselves, however, have a limited life before an excessive amount of nitrogen compounds (e.g., 1 ppm or more of nitrogen in the guard bed effluent) break through (or traverse) the entire bed without being adsorbed. Replacement of the nitrogen compound adsorptive material of the guard bed then becomes necessary to ensure that the guard bed effluent is sufficiently free of nitrogen, for example, to be introduced into a benzene alkylation catalyst bed or other catalyst bed that is susceptible to poisoning due to contact with nitrogen compounds. The operating life of the nitrogen guard bed material, such as a nitrogen adsorptive molecular sieve, is therefore an important consideration in the overall economics of styrene production and other processes where the removal of nitrogen compounds is beneficial or necessary.

SUMMARY OF THE INVENTION

Embodiments of the invention relate to the discovery that unsaturated aliphatic hydrocarbons such as olefinic compounds, and particularly diolefins, can shorten the effective life of adsorbents (e.g., nitrogen adsorptive zeolites or molecular sieves) used in nitrogen guard beds that are applied to various process streams, including recycle streams in styrene production processes. These unsaturated aliphatic (e.g., olefinic) compounds are present in aromatic process streams contaminated with nitrogen compounds, including benzene streams generated in the styrene process separation section and other streams requiring removal of the nitrogen compounds prior to being contacted with a catalyst or other material susceptible to nitrogen poisoning. The presence, in particular, of highly unsaturated olefinic compounds (e.g., $C_4$-$C_6$ diolefins) in aromatic streams (e.g., benzene streams) having nitrogen compound contaminants, adversely impacts the performance of nitrogen adsorptive materials. Without being bound by theory, it is believed that the olefinic compounds or other unsaturated aliphatic compounds react with aromatics such as benzene to form heavy reaction products that deposit on the nitrogen guard bed and shorten its life.

Other embodiments of the invention relate to the selective hydrogenation (or selective saturation) of unsaturated aliphatic (e.g., olefinic) compounds present in aromatic streams contaminated with nitrogen compounds and for which nitrogen removal is beneficial. The selective hydrogenation of these compounds (i.e., saturation of the olefinic compounds such as diolefins to a greater extent than the aromatic compounds) renders the hydrogenation effluent stream less reactive upon contact with the nitrogen guard bed, thereby prolonging its useful life. The combination of selective hydrogenation and nitrogen removal of aromatic streams containing both unsaturated aliphatic (e.g., olefinic) and nitrogen compounds can therefore extend the life of (1) catalysts such as the benzene alkylation catalyst in a styrene production process (2) the nitrogen removal guard bed, generally directly upstream of this catalyst. Additionally, the selective hydrogenation of only the most reactive components of the aromatic liquid feed stream, namely the unsaturated aliphatic hydrocarbons such as olefinic compounds (e.g., diolefins), minimizes the loss of benzene or other desired aromatic compounds to be recycled and reacted. The selective hydrogenation may occur immediately upstream of the nitrogen removal, for example, if the benzene/toluene splitter column overhead stream is subjected to both of these operations prior to being recycled to a benzene alkylation reactor. Otherwise, the selective hydrogenation may be applied to a liquid stream that undergoes various other operations (e.g., processing by distillation) before passing to the nitrogen guard bed. This is the case, for example, when the entire EB dehydrogenation reactor effluent is the hydrogenation feed stream that is treated by selective hydrogenation and only the recovered benzene in the benzene/toluene splitter column overhead is passed to the nitrogen removal guard bed.

Further embodiments of the invention relate to the use of selective hydrogenation in combination with nitrogen removal in a process for the producing styrene, as described in greater detail below.

These and other aspects and features relating to the present invention are apparent from the following Detailed Description.

BRIEF DESCRIPTION OF THE DRAWING

FIG. 1 shows a representative separation section of a styrene production process.

DETAILED DESCRIPTION

The present invention relates to a method for treating a hydrogenation feed stream (e.g., a liquid stream) comprising an aromatic compound (e.g., benzene), one or more nitrogen compounds, and one or more unsaturated aliphatic compounds (e.g., olefinic compounds such as diolefins). The method comprises contacting the hydrogenation feed stream with a hydrogenation catalyst to selectively hydrogenate the unsaturated aliphatic compounds. As indicated above, selective hydrogenation refers to the conversion of these compounds to a greater extent than the aromatic compound or compounds in the hydrogenation feed stream. In a representative embodiment, at least about 60%, typically at least about 70%, and often at least about 85%, of the unsaturated aliphatic compounds (e.g., diolefins) are converted or hydrogenated (e.g., to their corresponding mono-olefins or paraffins) in the hydrogenation effluent, while at least about 90%, typically at least about 95%, and often substantially all (e.g., at least about 99%) of the aromatic compound is unconverted (e.g., to its corresponding cycloparaffin). Therefore, in the case of a representative hydrogenation feed stream comprising benzene in an amount of at least 90% by weight, the hydrogenation effluent stream may also comprise benzene in an amount of at least 90% by weight.

The conversion levels above may apply to the amount of diolefins in the hydrogenation feed stream. Alternatively, these conversion levels may apply to the combined amount of olefins and diolefins, or even to the total amount of unsaturated aliphatic hydrocarbons (which may be substantially the same as this combined amount). In the case of a mixture of aromatic compounds, then this extent of the aromatic compound conversion is the total conversion of all aromatics in the feed stream. The compositions of the hydrogenation feed stream and hydrogenation effluent stream, used to determine the conversion of unsaturated aliphatic compounds (such as diolefins) and aromatic compounds, may be based on the determination of stream compositions using standard analytical methods such as gas chromatography (GC).

The extent of conversion of the unsaturated aliphatic compounds (e.g., olefinic compounds such as diolefins) can also be based on the Bromine Number of the feed stream and hydrogenation effluent, determined according to ASTM D1159, which is a measure of the extent of olefinicity or degree of unsaturation (i.e., extent to which a sample can be brominated, in grams of bromine consumed/100 grams of sample). Alternatively, the Bromine Number may be the calculated, theoretical bromine consumption (in grams of bromine per 100 grams of sample) of $C_4$-$C_6$ olefins and diolefins, acetylene, and other unsaturated (non-aromatic) compounds (e.g., cyclopentadiene) in the hydrogenation feed stream, based on a GC analysis used to determine the weight percentages of these compounds.

A representative hydrogenation feed stream has a Bromine Number of at least about 0.03, typically in the range from about 0.03 to about 1.0, and often in the range from about 0.10 to about 0.75. As a result of the undergoing selective hydrogenation, the hydrogenation effluent Bromine Number is normally reduced to at most about 30%, and often from about 10% to about 30%, of the Bromine Number of the hydrogenation feed (e.g., liquid) stream entering the selective hydrogenation reactor.

The hydrogenation feed stream comprises one or more aromatic compounds and one or more unsaturated aliphatic compounds (e.g., diolefins), in addition to one or more nitrogen compounds. As discussed above, representative hydrogenation feed streams are liquid benzene-containing streams generated commercially in the production of styrene from ethylbenzene. These include the EB dehydrogenation reactor effluent stream, or a portion of this stream, as well as the overhead stream from the benzene/toluene splitter. In the latter case, the hydrogenation feed stream will comprise at least about 90%, and typically at least about 95%, by weight of benzene. For any hydrogenation feed stream comprising benzene, at least a portion of this benzene may be recovered from an EB dehydrogenation reactor effluent. Because the aromatic compound is substantially unconverted in the selective hydrogen process, the hydrogenation effluent stream may contain amounts of aromatic compounds that are comparable to the amounts in the hydrogenation feed stream (e.g., at least about 90% by weight of benzene).

Other types of suitable liquid hydrogenation feed streams may be those containing alkylaromatic hydrocarbons such as xylenes and para-xylene in particular. Major sources of para-xylene include mixed xylene streams that result from the refining of crude oil. Examples of such streams are those resulting from commercial para-xylene separation processes, from xylene isomerization processes, or from the separation of $C_8$ alkylaromatic hydrocarbon fractions derived from a catalytic reformate by liquid-liquid extraction and fractional distillation.

The unsaturated aliphatic compounds and particularly diolefins in the hydrogenation feed stream have the potential to result in a loss of operating life of the nitrogen guard bed, as discussed above. The selective hydrogenation of these compounds is therefore beneficial upstream of zeolitic or other nitrogen adsorptive materials. Unsaturated aliphatic hydrocarbons such as diolefins in liquid streams treated according to the process described herein are normally present in an amount of at least about 100 ppm, typically in the range from about 200 ppm to about 2000 ppm, and often from about 500 ppm to about 1500 ppm of total diolefins (or dienes). Representative diolefins are in the $C_4$-$C_6$ carbon number range and include 1,3-butadiene, 1,2-butadiene, 1,4-pentadiene, 2-methyl-1,3-butadiene, 1,3-pentadiene (both cis and trans isomers), 3-methyl-1,2-butadiene, 1,4-hexadiene, 2,3-dimethyl-1,3-butadiene, 1,3-hexadiene (both cis and trans isomers), and mixtures thereof. The hydrogenation feed stream may also comprise cyclic diolefins such as cyclopentadiene and/or methyl-cyclopentadiene. Acetylene and phenylacetylene may also be present in the hydrogenation feed stream, particularly in the case of a benzene stream obtained from the separation section of a styrene production process. Cyclic diolefins and phenylacetylene, which are similarly detrimental to the performance of a nitrogen guard bed in terms of limiting its capacity for nitrogen removal, are also normally hydrogenated at least to the extent discussed above with respect to the unsaturated aliphatic compounds.

The hydrogenation feed stream additionally comprises one or more nitrogen compounds, which may include any of the nitrogen-containing corrosion inhibitors and polymerization inhibitors discussed above. The total amount of nitrogen in the hydrogenation feed stream generally ranges from 100 ppb to 100 ppm by weight, and is often within the range from about 1 ppm to about 10 ppm, measured as total nitrogen by chemiluminescence (ASTM D4629). One nitrogen compound of particular interest is acetonitrile, which may alone contribute from about 1 ppm to about 5 ppm by weight of nitrogen in the hydrogenation feed stream.

Process conditions for the selective hydrogenation of unsaturated aliphatic compounds (e.g., olefinic compounds such as diolefins) in the hydrogenation feed stream include a temperature from about 50° C. (120° F.) to about 300° C. (570° F.) and a pressure from about 1 barg (15 psig) to about 52 barg (750 psig). In some cases the hydrogenation feed stream may contain sufficient dissolved hydrogen, or a sufficient amount of hydrogen may be available as hydrogen dissolved in the hydrogenation feed stream, combined with a gaseous hydrogen-containing fraction flowing with a liquid hydrogenation feed stream, so that supplemental or makeup hydrogen is not needed to carry out the selective hydrogenation. This may be the case, for example, when the EB dehydrogenation reactor effluent stream (i.e., the feed to the separation section or distillation train) is selectively hydrogenated, since this stream contains hydrogen generated from the production of styrene, a portion of which may be present as a gaseous fraction.

In other embodiments, for example when the hydrogenation feed stream is an overhead stream from a benzene/toluene distillation column, a relatively small amount of hydrogen may be available. Therefore, in such cases a makeup hydrogen stream may be introduced to the selective hydrogenation process, for example by combining the makeup hydrogen with the hydrogenation feed stream to provide a molar ratio of hydrogen to olefin in the combined feed (hydrogen plus the hydrogenation feed stream, which may itself contain hydrogen) from about 0.5:1 to about 10:1, and often from about 1:1 to about 5:1. The makeup hydrogen, if used, may be combined with the hydrogenation feed stream prior to or during contacting this stream (e.g., a liquid) with the hydrogenation catalyst.

In some cases the amount of total hydrogen may be based on the stoichiometric amount of hydrogen needed for saturation of the unsaturated aliphatic compounds (olefins, diolefins, and alkynes such as acetylene), and possibly including other unsaturated compounds such as cyclopentadiene and/or phenylacetylene, in the hydrogenation feed stream. For example, the amount of hydrogen added should provide about 90% to about 500%, preferably about 100% to about 300% of the stoichiometric hydrogen requirement for saturation of these compounds. The amounts of hydrogen added based on the stoichiometric requirement thus correspond approximately to the molar "hydrogen:carbon-carbon double bond ratio" or the molar "hydrogen:degree of unsaturation ratio," where the degree of unsaturation refers to the total number of moles of carbon-carbon double bonds from the olefinic and diolefinic species, and where 100% of the stoichiometric hydrogen requirement corresponds to a molar ratio of 1.

The hydrogenation catalyst will generally comprise a metal such as nickel, palladium, platinum, or cobalt, alone or in mixtures, or in combination with other metals. The metal or metals are dispersed on a supporting material such as a refractory inorganic metal oxide, with alumina being representative.

In an overall process for removing or reducing the contents of both unsaturated aliphatic compounds (e.g., diolefins) and nitrogen in a hydrogenation feed stream containing an aromatic compound, the hydrogenation feed stream may be treated by selective hydrogenation as described above, followed by treatment of the hydrogenation effluent over a nitrogen guard bed, for example containing a zeolitic material. The removal of at least about 90% of the nitrogen compounds (e.g., as measured by chemiluminescence) with the guard bed generally results in a treated stream which can be processed over a catalyst that is sensitive to degradation or poisoning by nitrogen, such as the benzene alkylation catalyst in a commercial styrene production process. Often, in view of the high sensitivity of some catalyst systems to nitrogen poisoning, it is desired that the effluent from the nitrogen guard bed contain at most about 1 ppm of total nitrogen, and in some cases this requirement may be reduced to at most about 100 ppb or even at most about 10 ppb. Moreover, upstream of the guard bed, the conversion of at least about 60% of the olefins, diolefins, and acetylene in the hydrogenation feed stream effectively prolongs the life of the nitrogen guard bed (i.e., increases its nitrogen removal capacity) by reducing the extent of detrimental byproduct formation on the guard bed material.

In this manner, selective hydrogenation is performed to reduce the olefin, diolefin, and/or acetylene content of the hydrogenation feed stream, prior to nitrogen removal to yield the treated effluent stream (e.g., comprising at most about 1 ppm by weight of nitrogen). The selective hydrogenation reactor may be located immediately upstream of the nitrogen guard bed, although this is not necessary. For example, when the hydrogenation feed stream to the selective hydrogenation reactor is an EB dehydrogenation reactor effluent stream (upstream of the EB/styrene splitter), then one or more distillation separations, as discussed above, are performed on the hydrogenation effluent stream from this reactor, prior to treatment with the nitrogen guard bed. In this case, the nitrogen removal is typically applied only to the portion of the hydrogenation effluent having a high aromatic (e.g., benzene) content, such as the overhead stream of the benzene/toluene splitter. Otherwise, according to other embodiments only this overhead stream is subjected to selective hydrogenation, such that the entire hydrogenation effluent is treated with the nitrogen removal guard bed to yield a treated effluent stream having a reduced content of unsaturated aliphatic compounds such as diolefins (e.g., a reduced Bromine Number) and a reduced nitrogen content, which is subsequently introduced to a catalyst bed (e.g., the benzene alkylation catalyst bed).

FIG. 1 depicts a representative separation section of a styrene production process, which allows the recovery of various purified process streams from the EB dehydrogenation reactor effluent 10, or crude styrene product. This stream is produced as a result of dehydrogenating an ethylbenzene stream, which in turn is normally produced by reacting benzene with ethylene in a benzene alkylation reactor. The EB dehydrogenation reactor effluent 10 or crude styrene product comprises benzene (e.g., as unconverted benzene, added benzene, and/or byproduct benzene resulting from non-selective cracking reactions), nitrogen compounds (e.g., added to the process for corrosion/polymerization inhibition and/or recycled in the process), and unsaturated aliphatic compounds such as diolefins (e.g., reaction byproducts).

As discussed above, the entire EB dehydrogenation reactor effluent 10 may constitute a liquid hydrogenation feed stream to the selective hydrogenation process described herein, in which the hydrogenation effluent from this process is then sent to the normal distillation operations used in the separation section, such as those depicted in FIG. 1. In this case, the water content of the hydrogenation feed stream may be in the range from about 100 to about 2000 ppm, often from about 500 to about 1500 ppm by weight. In another representative embodiment, only a portion of the crude styrene product 10 is subjected to selective hydrogenation, prior to being sent to the separation section. One potential advantage of using the EB dehydrogenation reactor effluent 10 entirely or partly as the hydrogenation feed stream is that this stream contains dissolved hydrogen, and a gaseous fraction containing hydrogen may also be present. This hydrogen, produced as a result of the upstream dehydrogenation reaction, may therefore be conveniently available for the selective hydrogenation process, without the need for supplemental or makeup hydrogen addition.

According to other embodiments, the hydrogenation feed stream may be any of those normally recovered from the crude styrene product 10, including the process streams shown in the separation section depicted in FIG. 1. In a typical product recovery or separation section, crude styrene product 10 is fed to an EB/styrene splitter 21 used to fractionate this stream into an EB/light byproduct stream 16 and a styrene/heavy byproduct stream 14, with the latter stream typically being sent to a styrene column 27 to recover a purified styrene product stream 26 and reject a heavies stream 28 containing tar and other high-boiling residual components.

The EB/light byproduct stream 16 is sent to an EB recovery column 23 that separates this stream into a benzene/toluene overhead stream 20 and a purified EB stream 18 that is generally recycled to the upstream EB dehydrogenation reactor. The benzene/toluene overhead stream 20 may then be sent to a benzene/toluene distillation column or splitter 25, where the benzene/toluene splitter overhead stream 24 contains predominantly recovered benzene that is useful for recycle to the benzene alkylation reactor, while the benzene/toluene splitter bottoms stream 22 contains predominantly toluene.

A representative hydrogenation feed stream useful in the selective hydrogenation process described herein is therefore the benzene/toluene splitter overhead stream 24 of the benzene/toluene splitter 25, which normally comprises benzene together with nitrogen-containing corrosion and/or polymerization inhibitors, in addition to diolefins and other highly unsaturated hydrocarbons (e.g., acetylene). The water content of this stream is typically in the range from about 10 to about 1000 ppm, often from about 50 to about 500 ppm by weight. Another possible hydrogenation feed stream (recovered from the crude styrene product 10) for the selective hydrogenation process is the combined benzene/toluene overhead stream 20, particularly in the case where a benzene/toluene splitter is not used in the EB dehydrogenation effluent separation section. It will be appreciated that various process streams of the overall separation section depicted in FIG. 1, as well as other process streams generated from alternative flowschemes, will contain at least one aromatic compound, together with one or more nitrogen compounds and one or more unsaturated aliphatic compounds (e.g., diolefins) and will therefore be suitable for selective hydrogenation process described herein.

In view of this disclosure, the various considerations and tradeoffs involved in selecting a hydrogenation feed stream (e.g., a liquid stream) for selective hydrogenation, including the overall size of the stream, the contents of aromatics, nitrogen compounds, and unsaturated aliphatic hydrocarbons (e.g., diolefins and/or acetylene), the content of dissolved hydrogen (or the presence of free hydrogen), and the content of water, will become apparent to those skilled in the art.

Overall, aspects of the invention are directed to the use of selective hydrogenation, and particularly in combination with nitrogen removal, to treat process streams (e.g., for recycle to a nitrogen-sensitive catalyst bed). In view of the present disclosure, it will be seen that several advantages may be achieved and other advantageous results may be obtained. Those having skill in the art, with the knowledge gained from the present disclosure, will recognize that various changes could be made in the above processes without departing from the scope of the present disclosure. Mechanisms used to explain theoretical or observed phenomena or results, shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

EXAMPLE 1

Benzene Recovered from an EB Dehydrogenation Effluent Stream

A sample of a predominantly benzene stream recovered from an EB dehydrogenation effluent stream was analyzed for impurity levels using a standard analysis based on gas chromatography (GC). The analysis showed that this stream contained 1146 ppm by weight of diolefins in the $C_4$-$C_6$ carbon range, and in particular this represented the combined amount of the diolefins 1,3-butadiene, 1,2-butadiene, 1,4-pentadiene, 2-methyl-1,3-butadiene, 1-trans-3-pentadiene, 3-methyl-1,2-butadiene, cyclopentadiene, 1-cis-3-pentadiene, 1,4-hexadiene, 2,3-dimethyl-1,3-butadiene, trans-1,3-hexadiene, and cis-1,3-hexadiene. The stream also had 322 ppm by weight of mono-olefins in the $C_4$-$C_6$ carbon range and 3 ppm of acetylene. The Bromine Number of this liquid stream, determined according to ASTM D1159, was 0.29.

This liquid stream was representative of a benzene stream that would be treated for nitrogen removal using a nitrogen guard bed, prior to being recycled to a commercial benzene alkylation reactor. This stream was therefore also representative of a hydrogenation feed stream as described herein.

EXAMPLE 2

Selective Hydrogenation of Diolefins in a Model Hydrogenation Feed Stream

A model hydrogenation feed stream comprising benzene and approximating the diolefin and olefin content of a commercial benzene/toluene splitter overhead stream of the separation section of a styrene production process, as well as its nitrogen content, was prepared. The model liquid contained benzene with 1000 ppm of diolefins as either pentadiene or hexadiene, 300 ppm of mono-olefins as pentene, and 100 ppm of acetonitrile. The model hydrogenation feed stream was selectively hydrogenated by passing it over a palladium containing catalyst at 120° C. (248° F.) and 28 barg (400 psig) and at a liquid hourly space velocity (LHSV) of 25 $hr^{-1}$. Hydrogen was added in at a molar ratio of 5.0, based on the total moles of diolefins (dienes) and acetonitrile in the hydrogenation feed stream. The conversion of the diolefins was 92.9%, while saturation of the benzene was negligible.

EXAMPLE 3

Nitrogen Removal from a Commercial Benzene/Toluene Splitter Overhead Stream

The predominantly benzene stream recovered from an EB dehydrogenation effluent stream (namely a commercial benzene/toluene splitter overhead stream, obtained from the separation section of a styrene production process), as described in Example 1, was treated with a zeolitic guard bed to remove nitrogen. Table 1 below shows the analysis of this stream, both before and after this treatment.

TABLE 1

| Stream | Nitrogen Guard Bed Inlet | Nitrogen Guard Bed Outlet |
|---|---|---|
| Aromatics Distribution (wt %) | | |
| Benzene | 99.472 | 99.473 |
| Toluene | 0.309 | 0.313 |
| Styrene | 0 | 0 |
| $C_8$ alkylbenzene | 0 | 0.004 |
| $C_9$ alkylbenzene | 0 | 0.034 |
| $C_{10}$ alkylbenzene | 0.003 | 0.014 |
| $C_{11}$+ alkylbenzene | 0.001 | 0.036 |
| Nonaromatics | 0.215 | 0.112 |
| Basic Nitrogen (wt %) | <0.001 | <0.001 |
| Nitrogen (wt ppm) | 3.2 | 1 |
| Sulfur (wt ppm) | <0.05 | <0.05 |
| Bromine Number (g Br/100 g) | 0.308 | 0.167 |
| Mono-olefin, ppm | 322 | |
| Di-Olefin, ppm | 1146 | |
| Acetylene, ppm | 3 | |

The analytical results above show that although the nitrogen content was reduced across the guard bed, there was still 1 ppm of nitrogen breakthrough, which could prematurely deactivate the benzene alkylation catalyst upon recycle to this section of the styrene production process. Additionally, the increase in $C_8$-$C_{11}$+ alkylbenzenes across the guard bed indicated that heavy, coke-forming species were generated, most likely from alkylation of the unsaturated species, such as mono-olefins and diolefins, with benzene. The reduction in Bromine Number in the guard bed outlet was evidence of this.

EXAMPLE 4

Analysis of Spent Adsorbent from the Nitrogen Guard Bed

Shortly after obtaining the nitrogen guard bed outlet stream analysis, showing nitrogen breakthrough in Example 3, the spent zeolitic adsorbent material was analyzed. The spent adsorbent had 0.38% nitrogen by weight, approximating the commercial adsorbent capacity for nitrogen (prior to nitrogen breakthrough). A comparison of the carbon, hydrogen, and nitrogen content of the spent adsorbent, with a fresh adsorbent sample, is shown in Table 2.

TABLE 2

| | Spent Nitrogen Guard Bed Adsorbent | Fresh Nitrogen Guard Bed Adsorbent |
|---|---|---|
| Carbon (wt %) | 15.8 | 0.12 |
| Hydrogen (wt %) | 2.17 | 0.8 |
| Nitrogen (wt %) | 0.38 | 0.05 |

However, when used to treat a model feed that does not contain unsaturated aliphatic compounds, namely benzene containing 20 ppm of nitrogen and 50-500 ppm of water, the same zeolitic guard bed adsorbent had a much greater nitrogen capacity, in the range of 0.8-1% nitrogen by weight. This demonstrates that the upstream removal of olefins and diolefins from the inlet stream to the nitrogen guard, by selective saturation, beneficially impacts the useful life of the nitrogen guard bed adsorbent.

The invention claimed is:

1. A method for treating a hydrogenation feed stream comprising one or more aromatic compounds, one or more nitrogen compounds, and one or more unsaturated aliphatic hydrocarbons, the method comprising contacting the hydrogenation feed stream with a hydrogenation catalyst to selectively hydrogenate the unsaturated aliphatic hydrocarbons thereby generating a hydrogenation effluent; and contacting the hydrogenation effluent with a zeolitic guard bed to remove at least a portion of the one or more nitrogen compounds, wherein the hydrogenation feed stream comprises benzene, the one or more unsaturated aliphatic hydrocarbons are diolefins present in an amount ranging from about 100 to about 2000 ppm by weight, and contacting of the hydrogenation feed stream with the hydrogenation catalyst provides a hydrogenation effluent stream in which at least about 80% of the diolefins in the hydrogenation feed stream are hydrogenated and at least about 90% of the benzene in the hydrogenation feed stream is unconverted.

2. The method of claim 1, wherein the hydrogenation feed stream comprises benzene in an amount of at least 90% by weight.

3. The method of claim 1, wherein the one or more unsaturated aliphatic hydrocarbons are $C_4$-$C_6$ diolefins.

4. The method of claim 3, wherein the $C_4$-$C_6$ diolefins are selected from the group consisting of 1,3-butadiene, 1,2-butadiene, 1,4-pentadiene, 2-methyl-1,3-butadiene, 1,3-pentadiene, 3-methyl-1,2-butadiene, 1,4-hexadiene, 2,3-dimethyl-1,3-butadiene, 1,3-hexadiene, and mixtures thereof.

5. The method of claim 1, wherein the one or more unsaturated aliphatic hydrocarbons are present in the hydrogenation feed stream in a total amount of at least about 100 ppm by weight.

6. The method of claim 1, wherein the hydrogenation feed stream has a nitrogen content from about 1 ppm to about 10 ppm by weight.

7. The method of claim 1, wherein the hydrogenation feed stream has a Bromine Number of at least about 0.030 g Br/100 g.

8. The method of claim 7, wherein the hydrogenation effluent stream has a Bromine Number of at most about 30% of the Bromine Number of the hydrogenation feed stream.

9. The method of claim 1, wherein one of the one or more nitrogen compounds is acetonitrile.

10. The method of claim 1, wherein the contacting of the hydrogenation feed stream with the hydrogenation catalyst is conducted under selective hydrogenation conditions including a temperature from about 50° C. (120° F.) to about 300° C. (570° F.) and a pressure from about 1 barg (15 psig) to about 52 barg (750 psig).

11. The method of claim 1, further comprising combining the hydrogenation feed stream with a makeup hydrogen stream, prior to or during contacting the hydrogenation feed stream with a hydrogenation catalyst.

12. The method of claim 11, wherein the makeup hydrogen stream is combined with the hydrogenation feed stream at a molar hydrogen:degree of unsaturation ratio from about 0.5:1 to about 10:1.

13. The method of claim 1, wherein the catalyst comprises a metal selected from the group nickel, palladium, platinum, cobalt, and mixtures thereof.

14. The method of claim 13, wherein the metal is dispersed over a refractory inorganic oxide.

15. The method of claim 1, wherein the hydrogenation feed stream is an ethylbenzene dehydrogenation reactor effluent stream.

16. The process of claim 15, wherein the hydrogenation feed stream is an overhead from a benzene/toluene distillation column.

17. A method for treating a hydrogenation feed stream comprising contacting the hydrogenation feed stream with a hydrogenation catalyst to selectively hydrogenate one or more unsaturated aliphatic hydrocarbons to generate a hydrogenated effluent stream wherein the hydrogenation feed stream comprises:
   A) one or more aromatic compounds comprising at least about 90%, by weight, benzene;
   B) one or more nitrogen compounds comprising from 100 ppb-100 ppm, by weight, measured as total nitrogen by chemiluminescence; and
   C) one or more unsaturated aliphatic hydrocarbons present in an amount ranging from about 100 to about 2000 ppm by weight; and
   passing the hydrogenated effluent stream to a nitrogen removal unit.

18. A method for treating a hydrogenation feed stream comprising contacting the hydrogenation feed stream with a hydrogenation catalyst to selectively hydrogenate one or more unsaturated aliphatic hydrocarbons to generate a hydrogenated effluent stream wherein the hydrogenation feed stream comprises:
   A) one or more aromatic compounds comprising at least about 95%, by weight, benzene;
   B) one or more nitrogen compounds comprising from about 1-about 5 ppm, by weight, acetonitrile; and
   C) one or more dienes present in an amount ranging from about 100 to about 2000 ppm by weight; and
   passing the hydrogenated effluent stream to a guard bed.

* * * * *